(12) United States Patent
Hagg

(10) Patent No.: US 8,585,685 B2
(45) Date of Patent: Nov. 19, 2013

(54) DEVICE FOR TREATMENT OF HUMAN OR ANIMAL TISSUE BY MEANS OF A MAGNETICALLY MOVABLE INSTRUMENT

(75) Inventor: Martin Hagg, Wannweil (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1384 days.

(21) Appl. No.: 12/298,474

(22) PCT Filed: Apr. 25, 2007

(86) PCT No.: PCT/EP2007/003659
§ 371 (c)(1),
(2), (4) Date: Oct. 24, 2008

(87) PCT Pub. No.: WO2007/124909
PCT Pub. Date: Nov. 8, 2007

(65) Prior Publication Data
US 2009/0105695 A1    Apr. 23, 2009

(30) Foreign Application Priority Data

Apr. 27, 2006  (DE) .................. 10 2006 019 680
Jun. 27, 2006  (DE) .................. 10 2006 029 455

(51) Int. Cl.
*A61B 17/00* (2006.01)
*H02K 1/12* (2006.01)

(52) U.S. Cl.
USPC .......................................... 606/1; 310/254.1

(58) Field of Classification Search
None
See application file for complete search history.

(56) References Cited

U.S. PATENT DOCUMENTS

| | | |
|---|---|---|
| 3,358,676 A | 12/1967 | Frei et al. |
| 4,970,656 A | 11/1990 | Lo et al. |
| 2002/0103430 A1* | 8/2002 | Hastings et al. ............... 600/411 |
| 2004/0019447 A1* | 1/2004 | Shachar ........................ 702/115 |
| 2005/0101946 A1 | 5/2005 | Govari et al. |
| 2005/0182315 A1 | 8/2005 | Ritter et al. |

FOREIGN PATENT DOCUMENTS

| | | |
|---|---|---|
| CA | 2 505 464 A1 | 10/2005 |
| JP | 8-117240 A | 5/1996 |
| JP | 2000-500059 A | 1/2000 |
| JP | 2004-208892 A | 7/2004 |
| WO | WO 98/11826 A1 | 3/1998 |
| WO | WO 99/18852 A1 | 4/1999 |
| WO | WO 9918852 A1 * | 4/1999 |

* cited by examiner

*Primary Examiner* — Cherie M Stanfield
(74) *Attorney, Agent, or Firm* — Dickstein Shapiro LLP

(57) ABSTRACT

A device for the treatment of human or animal tissue by means of a movable instrument is disclosed. The device comprises means for generating a magnetic stator field, in which the tissue is located. For example, the means for generating the magnetic stator field may be a magnetic resonance tomograph (MRT). At least one conductor loop is provided on or in the instrument, and a generator is provided for generating a current that flows through the conductor loop in order to generate a magnetic useful field, which, in conjunction with the stator field, generates a resulting action for applying a useful force to the instrument.

18 Claims, 2 Drawing Sheets

DEVICE FOR TREATMENT OF HUMAN OR ANIMAL TISSUE BY MEANS OF A MAGNETICALLY MOVABLE INSTRUMENT

CROSS-REFERENCE TO RELATED APPLICATIONS

This application claims the benefit of the filing date of International Patent Application No. PCT/EP2007/003659, filed Apr. 25, 2007, which claims the benefit of the filing date of German Patent Application No. 10 2006 019 680.5, filed Apr. 27, 2006, and German Patent Application No. 10 2006 029 455.6, filed Jun. 27, 2006. International Patent Application No. PCT/EP2007/003659, filed Apr. 25, 2007, is incorporated herein by reference in its entirety.

FIELD OF THE INVENTION

The invention relates generally to a device for the treatment of tissue, and more particularly to a device for treatment of human or animal tissue by means of a magnetically movable instrument.

BACKGROUND OF THE INVENTION

During the treatment of human or animal tissue, in particular during minimally invasive operations or even during therapies, instruments are often introduced into the body and have to be moved at a site of application. Additionally, it is often necessary to perform mechanical work at the site of application. Typical examples of this are the devitalisation and/or removal of tumour tissue. Another typical example is the treatment of a cholecystolithiasis (gall-bladder stone) or the removal of nephroliths from kidney tracts or urinary tracts. In many cases, working with an endoscope is problematical because the movement of the actual instrument seated at the distal end of the endoscope presents problems.

Accordingly, a device that facilitates the movement of an instrument within a body or an area of tissue without a mechanical connection to the exterior is desired.

SUMMARY

In disclosed embodiments, a commercially available device, for example a magnetic resonance tomograph (MRT) (e.g., a nuclear magnetic resonance tomograph), generates a strong, static magnetic field which is used, in conjunction with a separately generated magnetic field of a conductor loop through which current flows, to generate a force which is applied to the instrument. This force can in turn be used to move the instrument within the body or tissue and also to effect mechanical work on the tissue.

If an MRT is used, the entire treatment can be simultaneously observed using imaging techniques. Thus, "two birds are killed with one stone", because the magnetic field on the one hand forms the basis of the imaging technique and is used on the other for performing mechanical work.

Movement of an instrument within a body or an area of tissue without a mechanical connection to the exterior may be achieved by a device by means of a movable instrument. The device comprises a means (e.g., an MRT) for generating a magnetic stator field in which the tissue is located. The device further comprises at least one conductor loop on or in the instrument and a generator for generating a current that flows through the conductor loop in order to generate a magnetic useful field which, in conjunction with the stator field, generates a resulting action for applying a useful force to the instrument. An explicit means may be used to generate the required stator field. Accordingly, the means for generating the magnetic field is not restricted to an MRT.

Disclosed embodiments may include a plurality of conductor loops arranged respectively at a certain solid angle with respect to each other (e.g., three conductor loops arranged at a solid angle of 90° with respect to each other). The generator for supplying a current that passes through the conductor loops is provided and designed in such a way that the direction and magnitude of the useful force can be adjusted. This facilitates better "maneuvering" of the instrument.

In disclosed embodiments, the generator for generating an alternating current is designed so that the instrument can execute vibrations. It may be of advantage to design the generator in such a way that the frequency of the alternating current can be adjusted to a resonance frequency of the instrument. In order to utilize a mechanical resonance of this kind, it is possible to generate relative high vibration amplitudes even with a low energy input. If the generator is designed to supply an additional direct current component, a "net propulsion" can be generated so that, for example, the instrument does not have to overcome any static friction on the one hand but, on the other, experiences a propulsion component so that it may be maneuvered to a target site.

Alternatively (or additionally), it is possible to design the generator for generating a rotating field and the instrument in such a way that the instrument or drilling or milling parts located thereon may be caused to rotate. Different movement components or force components may coincide in such a way that in addition to a rotating movement, a vibrating (striking) movement occurs.

A magnetic resonance tomograph may be used for generating a stator field for an electrical machine to drive a surgical or therapeutic instrument.

BRIEF DESCRIPTION OF THE DRAWINGS

In the following discussion, example embodiments are explained in more detail with reference to the enclosed drawings.

DETAILED DESCRIPTION OF THE INVENTION

In the following description, the same reference numbers are used for identical parts and parts with identical functions.

Figure 1:
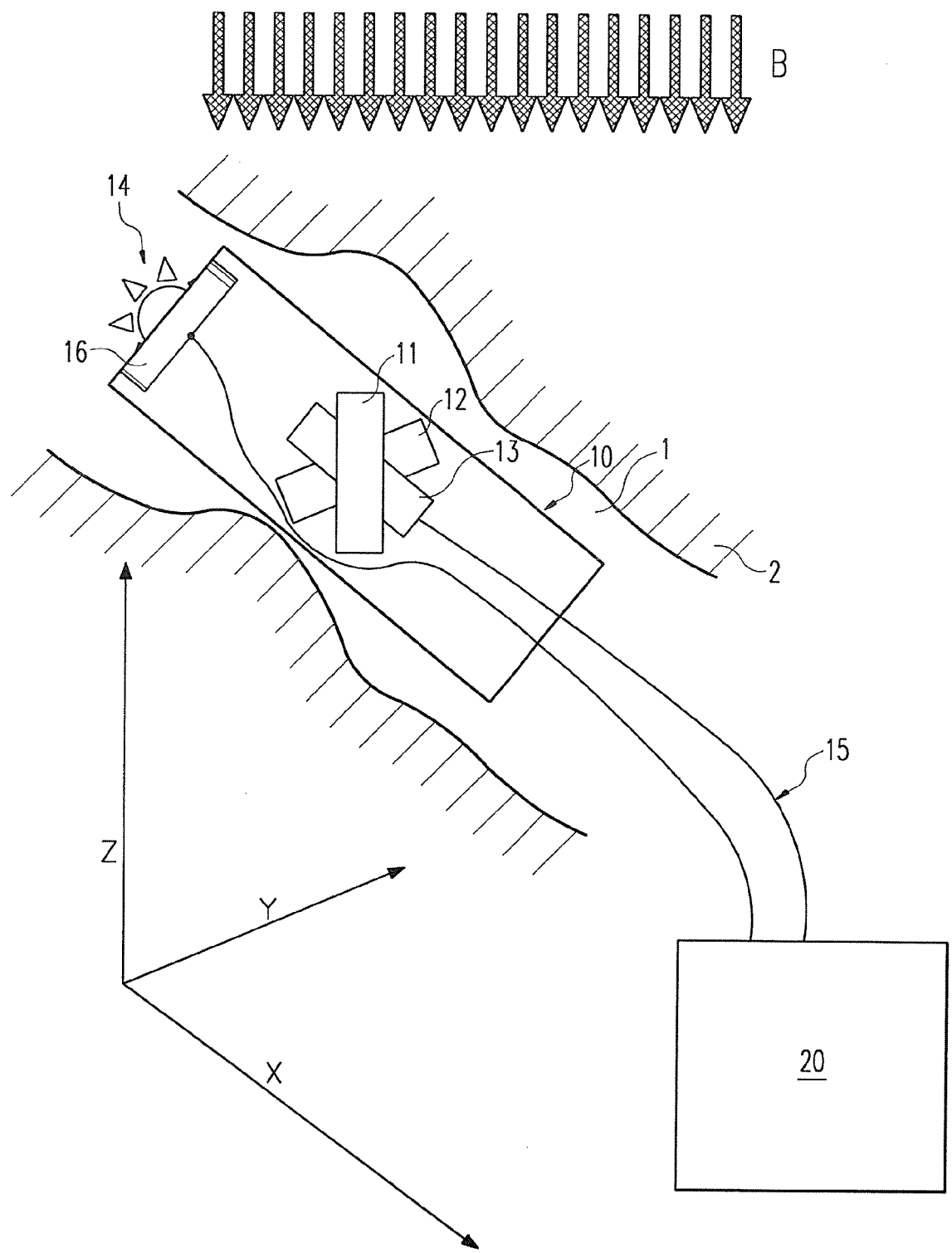
FIG. 1 is a schematic representation of a device being used in its "working environment" in accordance with a first embodiment disclosed herein.

In FIG. 1, a magnetic field B is generated by a magnetic resonance tomograph, for example, though persons skilled in the relevant art(s) will recognize that the magnetic field can be generated by a means explicitly provided therefor. A patient is located in the magnetic field B. The patient's tissue 2 is depicted as an area with a hollow organ 1, for example a ureter.

An instrument 10 is located in the hollow organ 1. Three conductor loops 11, 12 and 13, which are shown to be coils for illustrative purposes, are arranged in the interior of the instrument 10. The directions of the coils 11-13 are depicted schematically in the X, Y, Z coordinate system.

The three conductor loops 11-13 are connected by a lead 15 to a generator 20, which can pass current through each of the conductor loops 11-13 individually so that, in conjunction with the static magnetic field B, a resulting force forms on the instrument 10. The generator 10 may pass current through the conductor loops 11-13 in such a way that the instrument 10 on the one hand experiences a force component in the X-direction (that is in the direction of the hollow organ 1), and, on the other, this uniform force is superimposed by a vibration which causes the instrument 10 together with a milling head 14 located on its tip to vibrate in the direction of movement. Additionally, a torque can be generated by the application of a suitable rotating field to the conductor loops 11-13, so that the instrument 10 (or optionally only the milling head 14) rotates. In this way, for example, an object (e.g., a kidney stone) located in the hollow organ 1 can be comminuted.

In addition to the generation of the dynamic action with the aid of the static field B, an electromechanical transformer 16 (e.g., an ultrasonic vibrator) can be provided in the instrument 10. The generator 20 passes a current through the electromechanical transformer 16, causing the milling head 14 to vibrate (e.g., ultrasonically).

Figure 2:
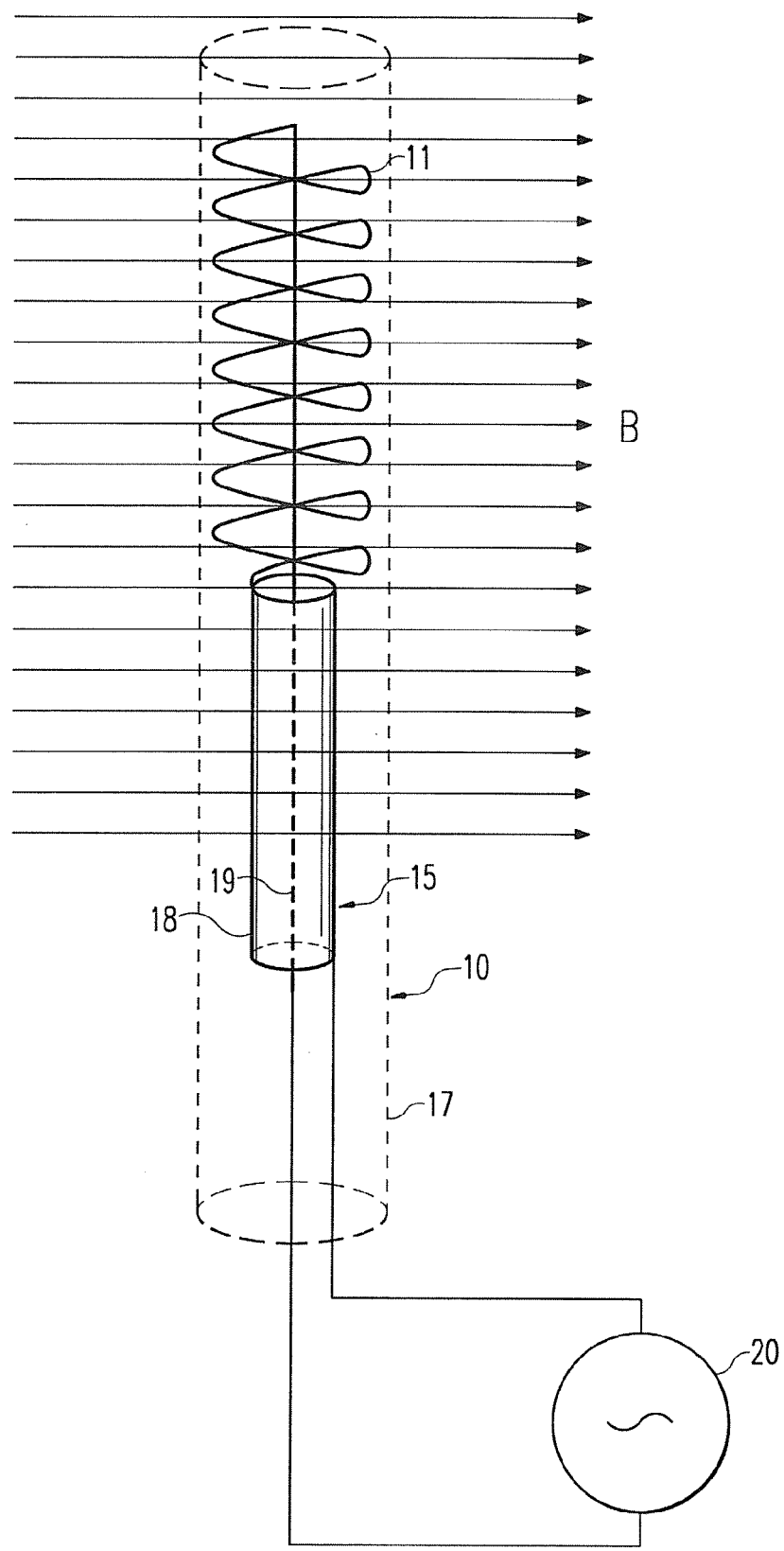
FIG. 2 is another schematic representation in accordance with a second embodiment disclosed herein.

In FIG. 2, the instrument 10 comprises a rod-shaped shaft 17 made of non-magnetic material on which the first conductor loop 11 is attached in the shape of a coil in an active region of the shaft 17 (in FIG. 2 at the upper end). The generator 20 supplies the first conductor loop 11 with alternating current via a coaxial lead 15 having an external conductor 18 and an internal conductor 19. The active region is located within the magnetic field B, which is permanently present in the nuclear magnetic resonance tomograph. The magnetic field B is considered to be homogeneous at least in the active region.

The active region experiences a torque in the clockwise or counterclockwise direction depending on the instantaneous current direction. The active region is deflected in the corresponding direction due to the elasticity of the shaft 17 (and parts of the device attached therein). The degree of the deflection is determined by the elasticity of the shaft 17, the magnitude of the current, the magnitude of the magnetic field, and the angle adopted by the axis of the conductor loop 11 with respect to the direction of the magnetic field lines.

Consequently, an alternating current flowing through the first conductor loop 11 can cause the active region to vibrate. With a suitable choice of current frequency, relatively high amplitudes can be generated with a relatively strong current in such a way that they correspond to the resonance frequency of the shaft 17, which is defined by the elasticity of the shaft 17 and the mass distribution within the shaft 17 (active region to inactive region).

The lead 15 may be constructed coaxially outside the active region, so that the Lorentz forces formed by the current flowing in the magnetic field cancel each other out.

In an embodiment, the instrument is designed as a needle-shaped probe, so that the active region is introduced into the target tissue to be treated. In this embodiment, the vibrations generated are transferred into the adjacent and surrounding tissue, so that the mechanically generated energy is converted into thermal energy there. The resulting heat can be used for the selective thermal devitalisation of tumour tissue, for example. The cell structures of the target tissue may be mechanically destroyed by the vibrations of a corresponding frequency in order to effect the devitalisation or defragmentation of the tissue.

It will be recognized by persons skilled in the relevant art(s) that the different individual ideas described above in connection with the first and second embodiments can be combined.

The invention claimed is:

1. A device for treatment of human or animal tissue by means of a movable instrument, comprising
    means for generating a magnetic stator field in which the tissue is located;
    at least one conductor loop on or in the instrument;
    a generator for generating a current that flows through the at least one conductor loop to generate a magnetic field, which, in conjunction with the stator field, generates a force upon the instrument; and
    a milling head coupled to the generator.

2. The device according to claim 1, wherein the at least one conductor loop includes three conductor loops arranged at 90° with respect to each other.

3. The device according to claim 1, wherein the generator is configured to generate an alternating current.

4. The device according to claim 3, wherein the generator is configured to be capable of adjusting a frequency of the alternating current to a resonance frequency of the instruments.

5. The device according to claim 3 wherein the generator is configured to generate the alternating current having a direct current component.

6. The device of claim 1, wherein the means for generating the magnetic stator field is a magnetic resonance tomograph.

7. The device according to claim 1, wherein the at least one conductor loop includes a plurality of conductor loops arranged at designated angles with respect to each other, and
    wherein the plurality of conductor loops and the generator are configured to enable adjustment of a direction and a magnitude of the force.

8. The device according to claim 3, wherein the generator is configured to supply a direct current in addition to generating the alternating current.

9. The device according to claim 3,
    wherein the generator is configured to generate a rotating field, and
    wherein the generator and the instrument are configured to be capable of collaboratively rotating the milling head.

10. A device for treatment of human or animal tissue by means of a movable instrument, comprising
    means for generating a magnetic stator field in which the tissue is located;
    at least one conductor loop on or in the instrument;
    a generator for generating a current that flows through the at least one conductor loop to generate a magnetic field, which, in conjunction with the stator field, generates a force upon the instrument; and
    a drilling head coupled to the generator.

11. The device according to claim 10, wherein the at least one conductor loop includes three conductor loops arranged at 90° with respect to each other.

12. The device according to claim 10, wherein the generator is configured to generate an alternating current.

13. The device according to claim 12, wherein the generator is configured to be capable of adjusting a frequency of the alternating current to a resonance frequency of the instruments.

14. The device according to claim 12 wherein the generator is configured to generate the alternating current having a direct current component.

15. The device of claim 10, wherein the means for generating the magnetic stator field is a magnetic resonance tomograph.

16. The device according to claim 10, wherein the at least one conductor loop includes a plurality of conductor loops arranged at designated angles with respect to each other, and
    wherein the plurality of conductor loops and the generator are configured to enable adjustment of a direction and a magnitude of the force.

17. The device according to claim 12, wherein the generator is configured to supply a direct current in addition to generating the alternating current.

18. The device according to claim 12,
wherein the generator is configured to generate a rotating field, and
wherein the generator and the instrument are configured to be capable of collaboratively rotating the drilling head.

* * * * *

UNITED STATES PATENT AND TRADEMARK OFFICE
CERTIFICATE OF CORRECTION

PATENT NO.       : 8,585,685 B2
APPLICATION NO.  : 12/298474
DATED            : November 19, 2013
INVENTOR(S)      : Martin Hagg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1385 days.

Signed and Sealed this
Twenty-second Day of September, 2015

Michelle K. Lee
*Director of the United States Patent and Trademark Office*